United States Patent
Sumida

(10) Patent No.: US 10,245,354 B2
(45) Date of Patent: Apr. 2, 2019

(54) METHOD FOR MANUFACTURING HOLLOW NEEDLE-SHAPED BODY, AND HOLLOW NEEDLE-SHAPED BODY

(71) Applicant: TOPPAN PRINTING CO., LTD., Taito-ku (JP)

(72) Inventor: Tomoya Sumida, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 90 days.

(21) Appl. No.: 15/241,677

(22) Filed: Aug. 19, 2016

(65) Prior Publication Data

US 2016/0354521 A1 Dec. 8, 2016

Related U.S. Application Data

(63) Continuation of application No. PCT/JP2015/000761, filed on Feb. 18, 2015.

(30) Foreign Application Priority Data

Feb. 24, 2014 (JP) .................................. 2014-033063

(51) Int. Cl.
| | |
|---|---|
| A61L 31/06 | (2006.01) |
| A61M 37/00 | (2006.01) |
| B81B 1/00 | (2006.01) |
| B81C 1/00 | (2006.01) |
| C08J 7/12 | (2006.01) |

(52) U.S. Cl.
CPC ......... *A61L 31/06* (2013.01); *A61M 37/0015* (2013.01); *B81B 1/008* (2013.01); *B81C 1/00111* (2013.01); *C08J 7/123* (2013.01); *A61M 2037/003* (2013.01); *A61M 2037/0023* (2013.01); *A61M 2037/0053* (2013.01); *B81B 2201/055* (2013.01); *C08J 2367/04* (2013.01)

(58) Field of Classification Search
CPC ............... A61L 31/06; A61M 37/0015; A61M 2037/0023; A61M 2037/003; B81B 1/008; B81C 1/00111; C08J 7/123

USPC .......................................................... 606/272
See application file for complete search history.

(56) References Cited

FOREIGN PATENT DOCUMENTS

| JP | 2005-021677 A | | 1/2005 |
|---|---|---|---|
| JP | 2009-72271 A | | 4/2009 |
| JP | 2010-58384 A | | 3/2010 |
| JP | 2010-63666 A | | 3/2010 |
| JP | 2011-72695 A | | 4/2011 |
| JP | 2012-143423 | * | 8/2012 |
| JP | 2012-143423 A | | 8/2012 |
| JP | 2014-23697 A | | 2/2014 |
| WO | 2010051551 | * | 5/2010 |
| WO | 2010051551 A1 | * | 5/2010 |
| WO | WO 2014/017561 A1 | | 1/2014 |

OTHER PUBLICATIONS

Authors: Vineet Singh and Meena Tiwari; International Journal of Polymer Science, vol. 2010, Article ID 652719, 23 pages Title: Structure-Processing-Property Relationship of Poly(Glycolic Acid) for Drug Delivery Systems 1: Synthesis and Catalysis; Accepted Sep. 25, 2010. (Year: 2010).*
Unknown author, title: Layers of the skin (only pertinent portion), National cancer institute. Downloaded from https://training.seer.cancer.gov/melanoma/anatomy/layers.html, (Year: 2018).*
International Search Report dated Apr. 7, 2015 in PCT/JP2015/000761, filed Feb. 18, 2015.

* cited by examiner

*Primary Examiner* — Yanzhi Zhang
(74) *Attorney, Agent, or Firm* — Oblon, McClelland, Maier & Neustadt, L.L.P.

(57) ABSTRACT

A method for manufacturing a hollow needle-shaped body includes producing a needle-shaped body having a substrate and a projection on a first surface of the substrate, and applying a laser beam to a second surface of the substrate opposite to the first surface such that a through hole that penetrates through the substrate and the projection is formed. The substrate and the projection are comprised of crystallized polyglycolic acid.

20 Claims, 2 Drawing Sheets

METHOD FOR MANUFACTURING HOLLOW NEEDLE-SHAPED BODY, AND HOLLOW NEEDLE-SHAPED BODY

CROSS-REFERENCE TO RELATED APPLICATIONS

The present application is a continuation of International Application No. PCT/JP2015/000761, filed Feb. 18, 2015, which is based upon and claims the benefits of priority to Japanese Application No. 2014-033063, filed Feb. 24, 2014. The entire contents of these applications are incorporated herein by reference.

BACKGROUND OF THE INVENTION

Field of the Invention

The present invention relates to a method for manufacturing a hollow needle-shaped body and relates to a hollow needle-shaped body.

Discussion of the Background

In recent years, a drug administration method as an alternative to injection has been attracting attention. The method uses an array made up of a plurality of needle-shaped bodies of a micron order of size to pierce the skin, and allows for direct administration of the drug into the skin.

The needle-shaped body must be made of a material which is harmless to the body even if the needle-shaped body is broken and remains in the body. Materials with potential for use in the needle-shaped body include biocompatible resins such as medical grade silicone, maltose, polylactic acid, polyglycolic acid and dextran (for example, see PTL 1).

Further, the aforementioned needle-shaped body may also be a hollow type having a through hole (hereinafter, also referred to as "hollow needle-shaped body"). For example, a method for forming the through hole in the hollow needle-shaped body is disclosed which includes forming the needle-shaped body having a substrate and a projection formed on one surface of the substrate from a resin material by a thermal imprint method, and then forming the through hole that penetrates through the substrate and the projection in a thickness direction of the substrate by radiating a laser beam onto the other surface of the substrate (for example, PTL 2).
PTL 1: JP-A-2005-21677
PTL 2: JP-A-2011-72695

SUMMARY OF THE INVENTION

According to one aspect of the present invention, a method for manufacturing a hollow needle-shaped body includes producing a needle-shaped body having a substrate and a projection on a first surface of the substrate, and applying a laser beam to a second surface of the substrate opposite to the first surface such that a through hole that penetrates through the substrate and the projection is formed. The substrate and the projection are comprised of crystallized polyglycolic acid.

According to another aspect of the present invention, a hollow needle-shaped body includes a substrate, and a projection formed on a surface of the substrate. The substrate and the projection have a through hole that penetrates through the substrate and the projection and are comprised of crystallized polyglycolic acid.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
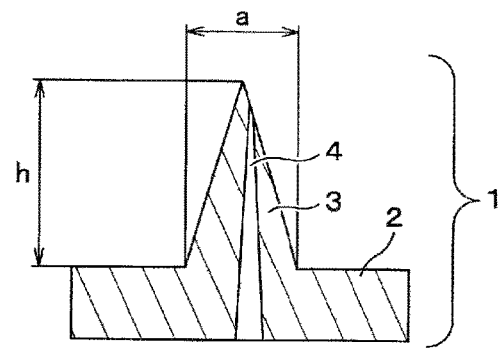
FIG. 1 is a cross sectional view which shows a configuration of a hollow needle-shaped body according to an embodiment of the present invention.

The embodiments will now be described with reference to the accompanying drawings, wherein like reference numerals designate corresponding or identical elements throughout the various drawings.

In the following detailed description, many specific details are set forth in order to provide a thorough understanding of the embodiments of the present invention. However, it should be obvious that those specific details are not necessarily indispensable to carry out one or more embodiments. Furthermore, for simplicity of illustration, known configurations and devices are schematically shown.

With reference to the drawings, embodiments of the present invention will be described.
(Configuration)

First, a configuration of a hollow needle-shaped body 1 will be described.

As shown in FIG. 1, the hollow needle-shaped body 1 includes a plate-shaped substrate 2, and a projection 3 formed on one surface (hereinafter, also referred to as "projection forming surface") of the substrate 2. The shape of the projection 3 is not specifically limited. For example, it may be conical shape, polygonal pyramid shape, round columnar shape or polygonal columnar shape. Furthermore, those shapes may be combined, for example, into a pencil-like shape, which is made up of a columnar shape and a conical shape stacked on the substrate 2 in this order. The hollow needle-shaped body 1 has a through hole 4 that penetrates through the substrate 2 and the projection 3 in a thickness direction of the substrate 2. The hollow needle-shaped body 1 (substrate 2, projection 3) is made of crystallized polyglycolic acid.

As described above, the hollow needle-shaped body 1 in this embodiment is made of biodegradable and biocompatible crystallized polyglycolic acid (that is, polyglycolic acid). Accordingly, even if the hollow needle-shaped body 1 is broken and remains in the body, it may cause less harm to the body.

The projection 3 of the hollow needle-shaped body 1 according to the present embodiment preferably has a height h in the range between 0.5 mm or more and 2.0 mm or less, more preferably, in the range between 0.7 mm or more and 1.5 mm or less. The term "height h" as used herein refers to the height from the surface of the substrate 2 on which the projection 3 is formed to the apex of the projection 3.

Further, when the maximum diameter of the projection 3 at a connection between the projection 3 and the substrate 2 of the hollow needle-shaped body 1 is defined as a maximum diameter a, a value h/a, is preferably in the range between 1.1 or more and 5 or less.

Furthermore, a plurality of projections 3 may be provided on the substrate 2. The number of projections 3 on the substrate 2 is preferably in the range between 1 or more and 50 or less, more preferably, in the range between 1 or more and 10 or less. The plurality of projections 3 on the substrate 2 can provide the advantageous effect of pain mitigation during drug administration, but may cause leakage of the drug during drug administration.

(Manufacturing Method)

Next, a method for manufacturing the hollow needle-shaped body 1 will be described.

Figure 2A:
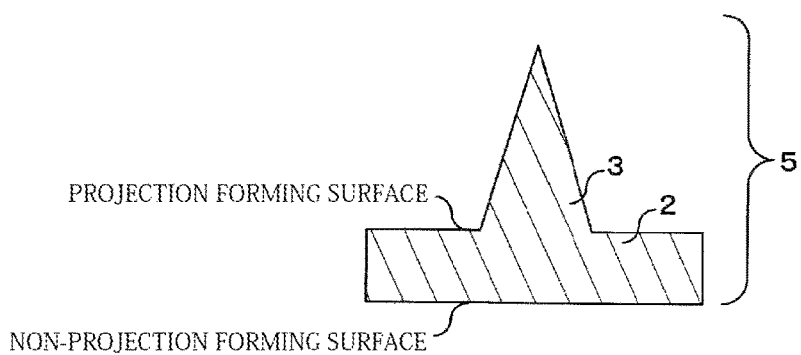
FIGS. 2(a) and 2(b) are cross sectional views which show a method for manufacturing the hollow needle-shaped body according to an embodiment of the present invention.

As shown in FIG. 2(a), a step (hereinafter, referred to as "first step") is first performed to manufacture a needle-shaped body 5 having the substrate 2 and the projection 3 formed on one surface (projection forming surface) of the substrate 2. A variety of known methods can be used to manufacture the needle-shaped body 5. For example, the methods include injection molding, compression molding, extrusion molding, thermal imprinting and hot embossing.

Further, the material for the needle-shaped body 5 (substrate 2, projection 3) is crystallized polyglycolic acid. Polyglycolic acid is a resin that relatively easily crystallizes. Crystallization methods include, for example, slowly cooling after heat molding, keeping at around the crystallization temperature (approximately 100 to 120° C.) for a certain period of time during cooling, and applying heat treatment at around the crystallization temperature after heat molding. Crystallization of polyglycolic acid can be seen by observing the color tone. Polyglycolic acid is transparent when it is not crystallized, and is not transparent (is white in color) when it is crystallized.

Furthermore, the crystallization of polyglycolic acid in this embodiment can be determined by measuring the degree of crystallization by using differential scanning calorimetry (DSC). When the degree of crystallization observed by differential scanning calorimetry (DSC) is 40% or more, the hollow needle-shaped body 1 made of polyglycolic acid according to the present embodiment is determined to be "crystallized". Although a higher degree of crystallization is preferable, the degree of crystallization is preferably not more than 90% considering manufacturing processes.

Figure 2B:
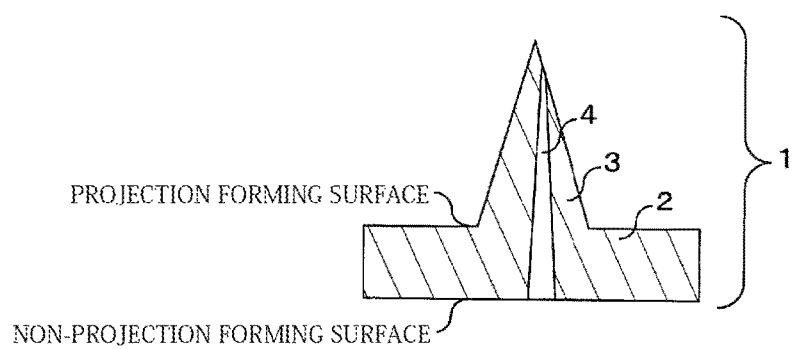

As shown in FIG. 2(b), the first step is followed by a step (hereinafter, referred to as "second step") of forming the through hole 4 that penetrates through the substrate 2 and the projection 3 in a thickness direction of the substrate 2 by radiating a laser beam onto the other surface (hereinafter, referred to as "non-projection forming surface") of the substrate 2. According to the present embodiment, the hollow needle-shaped body 1 having the through hole 4 is thus manufactured.

The inventor of the present invention has thoroughly studied to find that the through hole 4 can be formed in a good shape when a laser beam is radiated to crystallized polyglycolic acid, while the through hole 4 has defects in shape when a laser beam is radiated to non-crystallized polyglycolic acid. For example, there may be difficulty in forming the through hole 4 due to an effect of heat or the through hole 4 may have a lack of sharpness on the edge when it is formed.

According to the present embodiment as described above, the substrate 2 and the projection 3 are formed of crystallized polyglycolic acid which is suitable for laser processing. Accordingly, when the through hole 4 is formed in the substrate 2 and the projection 3 by radiating a laser beam, the through hole 4 can be formed in a good shape. In addition, since the laser beam is converged by a lens (not shown in the figure), a tapered cross section is formed. The cross sectional area of the through hole 4 decreases from the non-projection forming surface to the projection forming surface. As a result, the hollow needle-shaped body 1 can be formed in the shape suitable for liquid drug administration into the skin.

The type of the laser beam is not specifically limited. For example, an excimer laser beam which can be efficiently absorbed in the resin material and suppress the effect of heat can be advantageously used.

Figure 3:
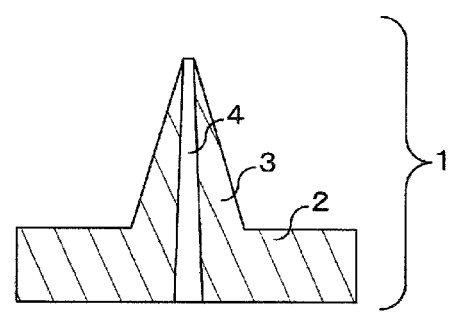
FIG. 3 is a cross sectional view which shows a modification example of the hollow needle-shaped body according to an embodiment of the present invention.

Although the through hole 4 in the example of the present embodiment is formed to penetrate the side surface of the projection 3 by radiating a laser beam (see FIG. 2(b)), other configurations are also possible. For example, as shown in FIG. 3, a through hole 4 that penetrates the apex of the projection 3 can be formed. Note that the hollow needle-shaped body 1 having the through hole 4 that penetrates the side surface of the projection 3 is more preferable than the hollow needle-shaped body 1 having the through hole 4 that penetrates the apex of the projection 3 in piercing ability of the hollow needle-shaped body 1 into the skin.

(Usage)

An example of usage of the hollow needle-shaped body 1 according to the present embodiment will be described.

In the usage of the hollow needle-shaped body 1 according to the present embodiment, that is, intradermal drug administration by using the hollow needle-shaped body 1, the hollow needle-shaped body 1 is first pierced into the skin. Then, a drug is administered into the skin via the through hole 4 of the hollow needle-shaped body 1. After that, the hollow needle-shaped body 1 pierced into the skin is withdrawn.

The above intradermal administration method is advantageous over other administration methods in that the liquid drug can be used in a similar manner to the conventional injection, the dose of drug can be increased, the dose of drug can be accurately controlled, and so on.

In the conventional drug administration method, a drug such as a vaccine is administered into the body by injection. Although injection is a safe administration method, it often involves severe pain when the injection needle is deeply pierced into the body to deliver the drug into the subcutaneous tissue. Further, in developing countries and the like, there are issues such as infection by reuse of injection needles and a high risk of occurrence of needle stick injuries.

ADVANTAGEOUS EFFECT OF EMBODIMENT

According to the present embodiment, the method for manufacturing the hollow needle-shaped body 1, and the hollow needle-shaped body 1, have the following advantageous effects.

(1) The method for manufacturing the hollow needle-shaped body 1 according to the present embodiment includes a first step of manufacturing the needle-shaped body 5 having the substrate 2 and the projection 3 formed on one surface (projection forming surface) of the substrate 2, and a second step of forming the through hole 4 that penetrates through the substrate 2 and the projection 3 by radiating a laser beam onto the other surface (non-projection forming surface) of the substrate 2. The substrate 2 and the projection 3 are made of crystallized polyglycolic acid.

In this configuration, the substrate 2 and the projection 3 are formed of crystallized polyglycolic acid which is suitable for laser processing. Accordingly, when the through hole 4 that penetrates through the substrate 2 and the projection 3 is formed by radiating a laser beam, the through hole 4 can be formed in a good shape.

(2) The method for manufacturing the hollow needle-shaped body 1 according to the present embodiment uses an excimer laser as a laser beam.

In this configuration, an excimer laser beam which can be efficiently absorbed in the resin material and suppress the effect of heat is radiated. Accordingly, the through hole 4 can be appropriately formed in the substrate 2 and the projection 3.

(3) In the method for manufacturing the hollow needle-shaped body 1 according to the present embodiment, the needle-shaped body 5 which is necessary for manufacturing the hollow needle-shaped body 1 is formed by transfer molding such as injection molding, imprinting and casting.

In this configuration, the hollow needle-shaped body 1 which is a micro structure can be manufactured at low cost in mass production.

(4) The hollow needle-shaped body 1 according to the present embodiment includes the substrate 2, the projection 3 formed on one surface (projection forming surface) of the substrate 2, and the through hole 4 which penetrates through the substrate 2 and the projection 3, wherein the substrate 2 and the projection 3 are made of crystallized polyglycolic acid.

In this configuration, the hollow needle-shaped body 1 is made of biodegradable and biocompatible polyglycolic acid. Accordingly, even if the hollow needle-shaped body 1 is broken and remains in the body, it may cause less harm to the body.

(5) The projection 3 of the hollow needle-shaped body 1 according to the present embodiment has the height h, which is for example in the range between 0.5 mm or more and 2.0 mm or less. Further, the height h divided by the maximum diameter a of the projection 3, the value (h/a), is for example in the range between 1.1 or more and 5 or less.

In general, the shape of the needle-shaped body needs to have a thinness and a tip angle sufficient for piercing the skin and a length sufficient for intradermal drug delivery (that is, sufficient height h). Accordingly, the projection 3 desirably has a length that penetrates through the stratum corneum which is the outermost layer of the skin but does not reach the nerve plexus, which is the height being specifically in the order of several hundreds of micrometers to several millimeters. Further, the needle-shaped body desirably has a diameter in the order of several tens of micrometers to several hundreds of micrometers.

In the hollow needle-shaped body 1 according to the present embodiment, it is possible to mitigate the pain felt by a patient during piercing the projection 3 into the skin since the length of the projection 3 is controlled not to reach the nerve cells in the dermis layer. Further, when vaccine is intradermally administered using the hollow needle-shaped body 1, the amount of vaccine used can be reduced compared with subcutaneous injection since antigen presenting cells are abundant in the skin.

(6) The hollow needle-shaped body 1 according to the present embodiment has the degree of crystallization of crystallized polyglycolic acid of 40% or more.

In this configuration, a sufficient strength can be applied to the hollow needle-shaped body 1.

(7) The hollow needle-shaped body 1 according to the present embodiment is a needle-shaped body having a through hole 4, and can be used for intradermal administration by piercing the needle-shaped body into the skin and delivering the drug into the skin via the through hole 4. The intradermal administration method is advantageous over other administration methods in that the liquid drug can be used in a similar manner to the conventional injection, the dose of drug can be increased, the dose of drug can be accurately controlled, and so on.

EXAMPLE

Examples of the hollow needle-shaped body 1 according to the present embodiment and a comparative example will be described.

Example 1

First, as shown in FIG. 2(a), the needle-shaped body 5 which was made of crystallized polyglycolic acid and included the substrate 2 and the projection 3 formed on one surface (projection forming surface) of the substrate 2 was fabricated by a thermal imprint method by using a nickel mold which was manufactured by machining. The substrate 2 was disk-shaped with a diameter of 10 mm and a thickness of 700 µm. The projection 3 was a rectangular pyramid shape with the height h of 800 µm. Furthermore, in the needle-shaped body 5, the projection 3 at the connection between the projection 3 and the substrate 2 had a square shape and a length of each side of the square was 350 µm. In the thermal imprint process, the needle-shaped body 5 was kept at around the crystallization temperature (110° C.) for a period of 5 minutes during cooling.

The entire needle-shaped body 5 thus fabricated in Example 1 was white in color. This revealed that polyglycolic acid was crystallized. Further, in the needle-shaped body 5 according to Example 1, the degree of crystallization of polyglycolic acid measured by using differential scanning calorimetry (DSC) was 55%.

After the needle-shaped body 5 was fabricated, the through hole 4 that penetrated through the substrate 2 and the projection 3 was formed as shown in FIG. 2(b) by radiating a KrF excimer laser beam from the non-projection forming surface. Thus, the hollow needle-shaped body 1 having the through hole 4 was formed. Further, the through hole 4 had a diameter of 100 µm on the non-projection forming surface, and 50 µm on the projection forming surface. The through hole 4 had a good shape with a sharp edge both on the non-projection forming surface and projection forming surface.

Example 2

First, as shown in FIG. 2(a), the needle-shaped body 5 which was made of crystallized polyglycolic acid and included the substrate 2 and the projection 3 formed on one surface (projection forming surface) of the substrate 2 was fabricated by a thermal imprint method by using a nickel mold which was manufactured by machining. The substrate 2 was disk-shaped with a diameter of 10 mm and a thickness of 700 µm. The projection 3 was a rectangular pyramid shape with the height h of 800 µm. Furthermore, in the needle-shaped body 5, the projection 3 at the connection between the projection 3 and the substrate 2 had a square shape and the length of each side of the square was 350 µm. In the thermal imprint process, the needle-shaped body 5 was kept at around the crystallization temperature (110° C.) for a period of 15 minutes during cooling.

The entire needle-shaped body 5 thus fabricated in Example 2 was white in color. This revealed that polyglycolic acid was crystallized. Further, in the needle-shaped body 5 according to Example 2, the degree of crystallization of polyglycolic acid measured by using differential scanning calorimetry (DSC) was 80%.

After the needle-shaped body 5 was fabricated, the through hole 4 that penetrates through the substrate 2 and the projection 3 was formed as shown in FIG. 2(b) by radiating a KrF excimer laser beam from the non-projection forming surface. Thus, the hollow needle-shaped body 1 having the through hole 4 was formed. Further, the through hole 4 had a diameter of 100 μm on the non-projection forming surface, and 50 μm on the projection forming surface. The through hole 4 had a good shape with a sharp edge both on the non-projection forming surface and projection forming surface.

Comparative Example

As a comparative example, the needle-shaped body 5 was fabricated in a similar manner to Example 1 except for "keeping at around the crystallization temperature (110° C.) for a period of 5 minutes during cooling" in Example 1.

Specifically, as shown in FIG. 2(a), the needle-shaped body 5 which was made of crystallized polyglycolic acid and included the substrate 2 and the projection 3 formed on one surface (projection forming surface) of the substrate 2 was fabricated by a thermal imprint method by using a nickel mold which was manufactured by machining. The substrate 2 was disk-shaped with a diameter of 10 mm and a thickness of 700 μm. The projection 3 was a rectangular pyramid shape with the height h of 800 μm. Furthermore, in the needle-shaped body 5, the projection 3 at the connection between the projection 3 and the substrate 2 had a square shape and the length of each side of the square was 350 μm.

The entire needle-shaped body 5 thus fabricated in Comparative Example was transparent. Further, in the needle-shaped body 5 according to Comparative Example, the degree of crystallization of polyglycolic acid measured by using differential scanning calorimetry (DSC) was 13%.

After the needle-shaped body 5 was fabricated, the through hole 4 that penetrated through the substrate 2 and the projection 3 was formed as shown in FIG. 2(b) by radiating a KrF excimer laser beam from the non-projection forming surface. Thus, the hollow needle-shaped body 1 having the through hole 4 was formed. In the hollow needle-shaped body 1 thus obtained, the through hole 4 had defects in shape with the edge widely expanded both on the non-projection forming surface and projection forming surface.

The conventional technique which forms the through hole that penetrates through the substrate and the projection by radiating a laser beam may have difficulty in forming the through hole due to an effect of heat generated by a laser beam. Further, if the through hole is formed, there may be defects in the shape of the through hole such as a lack of sharpness on the edge of the through hole.

The present invention can provide a method for manufacturing a hollow needle-shaped body having a through hole of a good shape and to provide a hollow needle-shaped body.

An aspect of the present invention is characterized by including: a first step of manufacturing a needle-shaped body having a substrate and a projection formed on one surface of the substrate; and a second step of forming a through hole that penetrates through the substrate and the projection by radiating a laser beam onto the other surface of the substrate after the first step, wherein the substrate and the projection are made of crystallized polyglycolic acid.

According to an aspect of the present invention, the substrate and the projection are formed of crystallized polyglycolic acid which is suitable for laser processing. Accordingly, when the through hole that penetrates through the substrate and the projection is formed by radiating a laser beam, the through hole can be formed in a good shape.

The present invention has been described above with reference to the specific embodiment. However, the above description is not intended to limit the present invention. When reading the description of the present invention, a person having ordinary skill in the art would obviously understand other embodiments of the present invention along with various modifications of the embodiment disclosed above. Therefore, the scope of the appended claims should be construed to cover modifications or embodiments included in the scope and spirit of the present invention.

REFERENCE SIGNS LIST

1 Hollow needle-shaped body
2 Substrate
3 Projection
4 Through hole
5 Needle-shaped body Obviously, numerous modifications and variations of the present invention are possible in light of the above teachings. It is therefore to be understood that within the scope of the appended claims, the invention may be practiced otherwise than as specifically described herein.

What is claimed is:
1. A hollow needle-shaped body, comprising:
a crystallized polyglycolic acid body having a substrate portion and at least one projection portion such that the projection portion is formed on a surface of the substrate portion,
wherein the crystallized polyglycolic acid body has a through hole penetrating through the substrate portion and the projection portion and is made of crystallized polyglycolic acid having a degree of crystallization in a range of 40% to 90%.

2. The hollow needle-shaped body of claim 1, wherein a height from the surface of the substrate portion to an apex of the projection portion is in a range of from 0.5 mm to 2.0 mm.

3. The hollow needle-shaped body of claim 2, wherein the crystallized polyglycolic acid body has the through hole penetrating through the substrate portion and the projection portion such that the through hole has a tapered cross section.

4. The hollow needle-shaped body of claim 2, wherein the height divided by a maximum diameter of the projection at a connection of the projection portion and the substrate portion is in a range of from 1.1 to 5.

5. The hollow needle-shaped body of claim 4, wherein the crystallized polyglycolic acid body has the through hole penetrating through the substrate portion and the projection portion such that the through hole has a tapered cross section.

6. The hollow needle-shaped body of claim 1, wherein the crystallized polyglycolic acid body has the through hole penetrating through the substrate portion and the projection portion such that the through hole has a tapered cross section.

7. The hollow needle-shaped body of claim 1, wherein a height from the surface of the substrate portion to an apex of the projection portion is in a range of from 0.7 mm to 1.5 mm.

8. The hollow needle-shaped body of claim 1, wherein the crystallized polyglycolic acid body has the through hole in a plurality.

9. The hollow needle-shaped body of claim 1, wherein the crystallized polyglycolic acid body has the through hole penetrating through the substrate portion and the projection portion such that the through hole penetrates a side surface of the projection portion.

10. The hollow needle-shaped body of claim 1, wherein the crystallized polyglycolic acid body has the through hole penetrating through the substrate portion and the projection portion such that the through hole penetrates an apex of the projection portion.

11. A method for manufacturing a hollow needle-shaped body, comprising:
   producing a crystallized polyglycolic acid body having a substrate portion and a projection portion formed on a first surface of the substrate portion; and
   applying a laser beam to a second surface of the substrate portion opposite to the first surface such that a through hole that penetrates through the substrate portion and the projection portion is formed,
   wherein the crystallized polyglycolic acid body is made of crystallized polyglycolic acid having a degree of crystallization in a range of 40% to 90%.

12. The method of claim 11, wherein the laser beam is an excimer laser beam.

13. The method of claim 12, wherein the crystallized polyglycolic acid body is produced such that a height from the first surface to an apex of the projection portion is in a range of from 0.5 mm to 2.0 mm.

14. The method of claim 13, wherein the crystallized polyglycolic acid body is produced such that the height divided by a maximum diameter of the projection portion at a connection of the projection portion and the substrate portion is in a range of from 1.1 to 5.

15. The method of claim 12, wherein the applying of the laser beam comprises applying the laser beam such that the crystallized polyglycolic acid body has the through hole having a tapered cross section.

16. The method of claim 11, wherein the crystallized polyglycolic acid body is produced such that a height from the first surface to an apex of the projection portion is in a range of from 0.5 mm to 2.0 mm.

17. The method of claim 16, wherein the crystallized polyglycolic acid body is produced such that the height divided by a maximum diameter of the projection portion at a connection of the projection portion and the substrate portion is in a range of from 1.1 to 5.

18. The method of claim 11, wherein the applying of the laser beam comprises applying the laser beam such that the crystallized polyglycolic acid body has the through hole having a tapered cross section.

19. The method of claim 16, wherein the applying of the laser beam comprises applying the laser beam such that the crystallized polyglycolic acid body has the through hole having a tapered cross section.

20. The method of claim 11, wherein the the crystallized polyglycolic acid body is produced such that a height from the first surface to an apex of the projection portion is in a range of from 0.7 mm to 1.5 mm.

* * * * *